United States Patent
Vaidya et al.

(10) Patent No.: US 10,445,465 B2
(45) Date of Patent: Oct. 15, 2019

(54) SYSTEM AND METHOD FOR EFFICIENT TRANSMISSION OF PATIENT DATA

(71) Applicant: GENERAL ELECTRIC COMPANY, Schenectady, NY (US)

(72) Inventors: Vivek Prabhakar Vaidya, Bangalore (IN); Hima Mukesh Patel, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 547 days.

(21) Appl. No.: 14/524,696

(22) Filed: Oct. 27, 2014

(65) Prior Publication Data
US 2015/0142462 A1 May 21, 2015

(30) Foreign Application Priority Data
Nov. 19, 2013 (IN) .......................... 5324/CHE/2013

(51) Int. Cl.
*G16H 40/40* (2018.01)
*G06F 19/00* (2018.01)

(52) U.S. Cl.
CPC ........ *G06F 19/3418* (2013.01); *G06F 19/321* (2013.01)

(58) Field of Classification Search
CPC ............... G06F 19/3418; G06F 19/345; G06T 2211/40; A61B 1/00; A61B 5/06; A61B 5/062; G16H 50/20
USPC .......................................................... 705/2
See application file for complete search history.

(56) References Cited

U.S. PATENT DOCUMENTS

| | | | |
|---|---|---|---|
| 7,244,230 B2 * | 7/2007 | Duggirala | A61B 8/00 600/300 |
| 8,069,057 B2 | 11/2011 | Choubey et al. | |
| 8,150,175 B2 | 4/2012 | Natanzon et al. | |
| 8,315,688 B2 | 11/2012 | Ueda | |
| 8,331,637 B2 | 12/2012 | Bar-Aviv et al. | |
| 8,386,278 B2 | 2/2013 | Maresh et al. | |
| 8,682,142 B1 * | 3/2014 | Boskovitz | G11B 27/034 386/278 |

(Continued)

OTHER PUBLICATIONS

Allcock et al., "Data Management and Transfer in High-Performance Computational Grid Environments", Elsevier Science Publishers, vol. No. 28, Issue No. 5, pp. 749-771, May 2002.

(Continued)

*Primary Examiner* — Hiep V Nguyen (74) *Attorney, Agent, or Firm* — Amin, Turocy & Watson, LLP (57) ABSTRACT

A method and system for communicating medical data is presented. Patient data, scan parameters, and/or reference information may be received from a patient unit communicatively coupled to a remote unit over a communication network. The patient data may include at least an image corresponding to a patient. Further, one or more anatomical regions in the image may be identified. Additionally, ranks corresponding to the one or more anatomical regions may be computed based on the patient data, the scan parameters, and/or the reference information. Further, one or more portions of the image corresponding to the one or more anatomical regions may be iteratively transmitted from the patient unit to the remote unit based on the computed ranks.

17 Claims, 4 Drawing Sheets

(56) References Cited

U.S. PATENT DOCUMENTS

| | | | |
|---|---|---|---|
| 9,116,734 B1* | 8/2015 | Twitchell, Jr. | G06F 9/45558 |
| 2006/0274928 A1* | 12/2006 | Collins | A61B 6/00 382/132 |
| 2008/0118131 A1* | 5/2008 | Skinner | G06T 7/0012 382/131 |
| 2010/0223276 A1 | 9/2010 | Al-Shameri et al. | |
| 2011/0289310 A1 | 11/2011 | Selgas et al. | |
| 2012/0070045 A1 | 3/2012 | Vesper et al. | |
| 2012/0265551 A1 | 10/2012 | Backhaus et al. | |
| 2013/0034279 A1 | 2/2013 | Cosatto et al. | |
| 2013/0110537 A1 | 5/2013 | Smith | |

OTHER PUBLICATIONS

"Image-Enabling The Enterprise", Carestream Health, Inc., pp. 1-8, Jul. 20, 2011.

\* cited by examiner

SYSTEM AND METHOD FOR EFFICIENT TRANSMISSION OF PATIENT DATA

BACKGROUND

Embodiments of the present specification relate generally to data transmission, and more particularly to systems and methods for real-time access to patient data from remotely connected systems.

Real-time access to comprehensive patient data, particularly during emergency situations, facilitates timely diagnosis and appropriate treatment of a patient. Accordingly, hospitals and other healthcare institutions store the patient data as electronic medical records (EMR) for use by authorized medical practitioners. Particularly, the EMR may correlate patient metadata with acquired diagnostic information to provide the medical practitioner with historical and current medical information for each patient.

Typically, the EMR may be stored, for example, in a hospital information system (HIS), a radiology information system (RIS), and/or a picture archiving and communication system (PACS) that is accessible to the medical practitioner. As the EMR includes privileged patient data, traditionally, an EMR storage and management system is often deployed in a designated system in the hospital premises. Evolution of telemedicine systems, however, has enabled access to traditional desktop-based healthcare systems including an EMR system from remotely located wireless, mobile, and/or wired systems.

Conventionally, telemedicine systems may provide specialized medical services over large geographical areas, including rural areas, where modern medical facilities and skilled medical practitioners have limited reach. Particularly, telemedicine systems provide a unique opportunity to shift specialized healthcare outside a traditional hospital setting to a patient in a clinic, in a home-centered setting and/or a remote unit setting. For example, a telemedicine system may allow a remotely located medical practitioner access to diagnostic resources, and previous and/or current patient data to allow expeditious detection of a patient condition and/or provision of appropriate treatment during medical emergencies.

Accordingly, certain healthcare institutions have extended access to select healthcare systems over wireless networks such that the patient data may be transmitted to authorized mobile devices such as laptops, tablets, cellular phones, and/or personal digital assistants (PDAs). Other healthcare institutions employ telemedicine solutions that provide access to certain medical instrumentation and applications via cloud-based servers rather than deploying these resources in the hospital premises. For example, a telemedicine solution may integrate computing, wireless networking, data storage, and/or middleware technology into a cloud-based architecture that may be remotely accessible to authorized medical practitioners. Use of such cloud-based architecture allows for reduction in energy and equipment costs, while also saving floor-space in the hospital premises.

However, there remains a gap between availability of conventional telemedicine systems and their practical implementation. Many of the conventional telemedicine systems, for example, rely on expensive proprietary hardware and/or dedicated wireless links, and thus, may not be scalable. Alternatively, certain telemedicine systems employ more widely available cellular communication links. The cellular communication links, however, may be affected by low data rates, congestion, and/or repeated interruption, thus limiting use of the cellular links in emergency situations. Furthermore, a large volume of patient data such as diagnostic images may further impede timely and robust delivery of life-critical medical data to a remotely located medical practitioner.

BRIEF DESCRIPTION

In accordance with certain aspects of the present specification, a method for communicating medical data corresponding to a patient is presented. The method includes receiving patient data, scan parameters, and/or reference information from a patient unit communicatively coupled to a remote unit over a communication network. The patient data may include at least an image corresponding to the patient. The method further includes identifying one or more anatomical regions in the image. Additionally, the method includes computing ranks corresponding to the one or more anatomical regions based on the patient data, the scan parameters, and/or the reference information. Further, the method also includes iteratively transmitting one or more portions of the image corresponding to the one or more anatomical regions from the patient unit to the remote unit based on the computed ranks In accordance with certain other aspects of the present specification, a system for communicating medical data corresponding to a patient is disclosed. The system includes a patient unit configured to acquire patient data, scan parameters, and/or reference information, where the patient data may include at least an image corresponding to the patient. The system further includes a remote unit communicatively coupled to the patient unit over a communication network. Further, the system also includes a network computing unit communicatively coupled to one or more of the patient unit and the remote unit, where the network computing unit is configured to identify one or more anatomical regions in the image, compute ranks corresponding to the one or more anatomical regions based on the patient data, the scan parameters, and/or the reference information, and iteratively transmit one or more portions of the image corresponding to the one or more anatomical regions from the patient unit to the remote unit based on the computed ranks

DRAWINGS

These and other features, aspects, and advantages of embodiments of the present specification will become better understood when the following detailed description is read with reference to the accompanying drawings in which like characters represent like parts throughout the drawings, wherein.

DETAILED DESCRIPTION

The following description presents methods and systems for efficient and timely communication of medical information. Particularly, the embodiments described herein describe exemplary methods and systems for identifying relevance of acquired medical information and expeditiously transmitting the medical information based on the identified relevance.

Conventionally, telemedicine systems lack a provision of customized quality-of-service (QoS) for effectively communicating different kinds of medical information. Large image files having low transmission priority, thus, may occupy a majority of an infrastructure bandwidth to the detriment of emergency telemedicine communications. In contrast, embodiments of the present specification describe methods and systems that prioritize and incrementally communicate subsets of acquired medical information over a communication network based on a corresponding relevance. Particularly, embodiments described hereinafter present exemplary methods and systems that prioritize transmission of the medical information to a remotely located medical specialist over a resource-constrained communication network, thereby facilitating faster diagnosis.

Although the following description includes only a few embodiments, the present specification may be implemented in many different operating environments and systems for communicating medical information. By way of example, embodiments of the present specification may be used in an edge medical device, a medical specialist's workstation, a mobile device, a router, and/or a hospital server that may be communicatively coupled to one or more types of communication networks. Particularly, in one embodiment, the present specification may be implemented in a cloud-based medical imaging system for intelligently communicating the medical information to a mobile device that may be remotely connected to the cloud-based imaging system.

Typically, mobile devices are disposed at the periphery of a network, such as the Internet. Unfortunately, the periphery of the network may experience more congestion as compared to a network core. Implementation of the present system in a mobile medical device, thus, may facilitate prioritization of real-time and mission-critical data packets at the network edges. In one exemplary implementation, indicative ranks may be dynamically computed for different portions of a diagnostic image. The dynamically computed ranks may then be used to determine an order of an intelligent incremental transmission of the different portions of the diagnostic image to a medical specialist over a designated communication link. Particularly, the dynamically computed ranks may be used to determine the order of transmission of the portions of the image based on a determined relevance of corresponding anatomical regions, prevailing network characteristics, and/or an urgency of a current situation.

By way of example, when using cellular networks for communicating medical information over a bandwidth-constrained communication link, the present system may be configured to segment a diagnostic image. Particularly, the image may be segmented to suit a bandwidth of an available communication link for transmission. The image segments may then be iteratively transmitted based on a relevance of corresponding anatomical regions to patient diagnosis.

In one embodiment, the present system may allow a user to specify certain input to selectively prioritize transmission of the different segments of the image. Additionally, the present system may also allow customization of content and/or quality characteristics of the image segments based on the relevance of corresponding anatomical regions. For example, certain segments corresponding to background regions of the image may be compressed to expedite delivery of the relevant portions of the image even over congested communication links, thereby extending a reach of quality medical services over a wider geographic area.

Although the present description is presented in the context of transmission of medical information, implementation of the present embodiments of the systems and methods described herein in non-medical applications is also contemplated. For example, embodiments of the present specification may be employed in other non-invasive imaging contexts, such as baggage screening, package screening and/or industrial nondestructive evaluation of manufactured parts. An exemplary environment that is suitable for practicing various implementations of the present specification will be discussed in greater detail in the following sections with reference to FIGS. 1-2.

Figure 1:
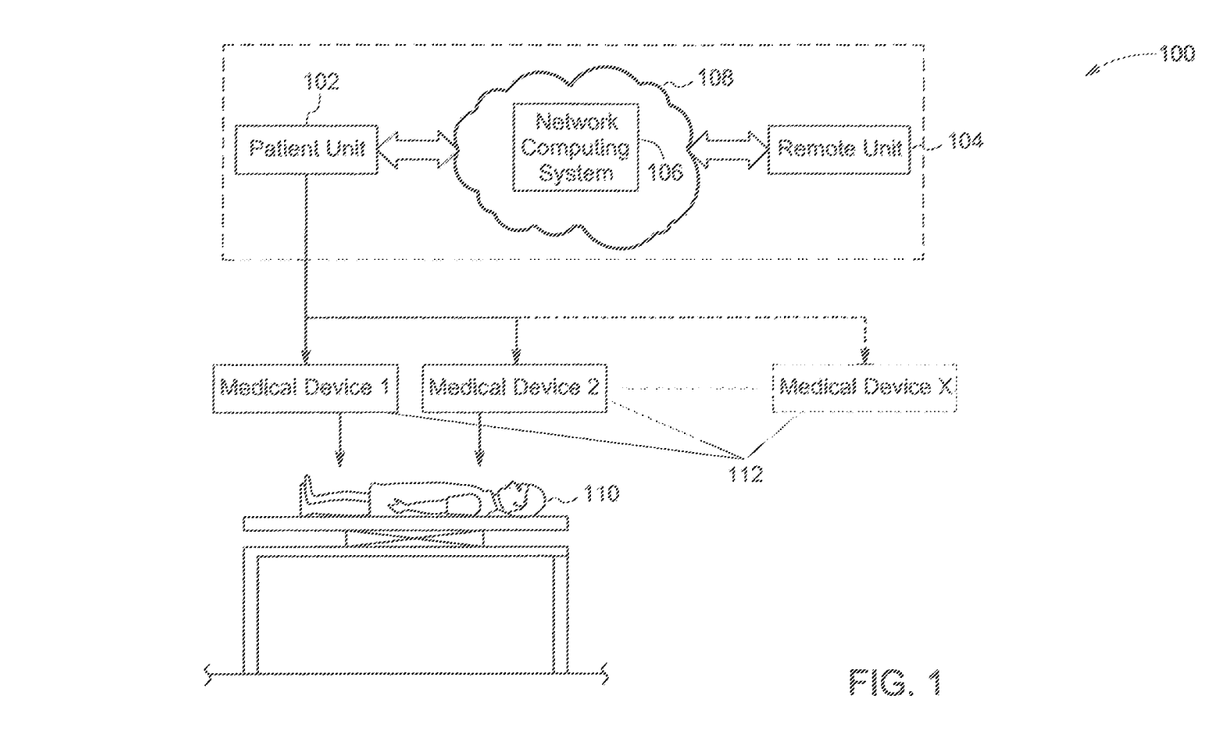
FIG. 1 is a schematic block diagram of an exemplary patient data communication system, in accordance with aspects of the present specification.

FIG. 1 illustrates an exemplary patient data communication system 100 configured to communicate diverse classes of medical information to and from a plurality of patient monitoring devices and/or diagnostic imaging devices (medical devices). Accordingly, the system 100 may be implemented, for example, in an image acquisition system, a mobile computing system, a desktop computer, a router, a cloud computing system, and/or a virtual server. Embodiments of the system 100, thus, may be configured to provide remote access to medical information at home, an emergency site, a medical practitioner's office, a military field site, an ambulance, a school, a nursing home, and/or an assisted living facility.

To that end, in one embodiment, the system 100 may include a patient unit 102, a remote unit 104, and a network computing system 106 communicatively coupled to each other through a wired and/or wireless communication network 108. In one embodiment, the patient unit 102 may include medical imaging systems such as a computed tomography (CT) system, a positron emission tomography (PET) scanner, a single photon emission computed tomography (SPECT) scanner, a magnetic resonance imaging (MRI) system, an ultrasound system, an X-ray system, and/or information systems such as HIS, RIS, and/or PACS. Further, the remote unit 104 may include a desktop computer, a specialist workstation, a laptop, a smartphone, and/or a tablet computing device.

In one embodiment, the system 100 may be configured to allow for efficient communication of data corresponding to a patient 110 from the patient unit 102 to the remote unit 104 for further evaluation by a medical specialist. As used herein, the term "patient" may be used to refer to any living person or animal. Further, the term "specialist" may be used to refer to a paramedic, a general physician, a medical practitioner who specializes in a particular field of medicine, or any person suited to provide medical consultation.

Additionally, as used herein, the term "patient data" may be used to refer to diagnostic images, previous patient reports, and/or patient profile information including, for example, a unique patient identifier (ID), age, sex, and/or demographics. The patient data may also include physiological information such as heart rate and respiration received from one or more medical devices 112 that may be operatively coupled to the patient 110. For example, the medical devices 112 may include an EKG system, a blood glucose monitor, a blood pressure monitor, an oxygen monitor, a magnetic resonance imaging (MRI) system, a computed tomography (CT) system, an ultrasound system, an X-ray machine, an intravenous monitor, and/or an anesthesia monitor. As used herein, the term "medical devices," however, may not be limited to specific medical equipment but may include peripheral devices used for medical purposes.

The peripheral devices, for example, may include a video device, an audio device, and/or other suitable devices such as temperature and pressure sensors that may be used to acquire information for use in diagnosing the patient 110.

Furthermore, in one embodiment, the patient unit 102 may be configured to acquire data corresponding to the patient 110 and transmit the acquired patient data to the remote unit 104 for allowing the specialist to diagnose the patient 110 based on the received patient data. In such an embodiment, the patient unit 102 may be configured to process the acquired patient data to generate, for example, diagnostic images and/or other medically useful information. The patient unit 102 may further be configured to transmit the diagnostic images and/or the medically useful information to the remote unit 104 for further evaluation.

In an alternative embodiment, however, the patient unit 102 may be configured to communicate the acquired patient data to the network computing system 106. The network computing system 106 may be configured to process the acquired patient data and generate corresponding diagnostic images and/or other medically useful information. Additionally, the network computing system 106 may be configured to transmit the diagnostic images and/or other medically useful information to the remote unit 104 for further evaluation. To that end, in certain embodiments, the network computing system 106 may correspond to a cloud computing system or a virtual server that may be remotely accessible to the specialist through the remote unit 104. Accordingly, use of the network computing system 106 may allow for transference of computationally intensive image reconstruction and processing from the patient unit 102 to the network computing system 106, thereby allowing use of a more cost-effective patient unit 102.

Although FIG. 1 illustrates only a single patient unit 102, a single remote unit 104, and a single network computing system 106, other embodiments may include any number of these devices to allow a plurality of medical systems to communicate with one or more specialists. For example, a single patient unit 102 including a CT system may be configured to communicate the patient data to a plurality of specialists for consultation. Alternatively, a single specialist may receive patient data from a plurality of patient units, for example, an MRI system and a CT system to diagnose a pathological condition of the patient 110.

Embodiments of the system 100, thus, may provide universal access to the patient data by allowing access between the multiple medical devices 112 and a facility or location where the patient data is processed, for example, the patient unit 102 and/or the network computing system 106. Accordingly, in one embodiment, one or more of the patient unit 102, the network computing system 106, and the remote unit 104 may be co-located in a hospital or a healthcare facility. In an alternative embodiment, however, one or more of the patient unit 102, the network computing system 106 and the remote unit 104 may be located at different locations such as a home, a healthcare facility, or a hospital and may be configured to communicate the patient data over the communication network 108.

In one embodiment, the communication network 108 may include wireless local area networks (WLAN), wide area networks (WAN) such as Worldwide Interoperability for Microwave Access (WiMax) networks, satellite networks, cellular networks, sensor networks, ad hoc networks, and/or short-range networks. In alternative embodiments, the communication network 108 may include wired networks or a hybrid of wireless and wired networks.

Furthermore, in certain embodiments, the system 100 may be configured to connect to different communication networks such as the communication network 108, thereby allowing the system 100 to switch between different communication networks to support transmission of the patient data. For example, in one embodiment, the system 100 may be configured to communicate the patient data over a WLAN. However, in case of interference or other disruption to a communication flow, the system 100 may be configured to evaluate other communication network options, for example, a short-range or an ad hoc network available in the vicinity for communicating the patient data. Particularly, the system 100 may be configured to communicate the patient data in an incremental and/or prioritized manner. Certain exemplary components of a patient data communication system configured to allow for incremental and/or prioritized patient data communications will be discussed in greater detail with reference to FIG. 2.

Figure 2:
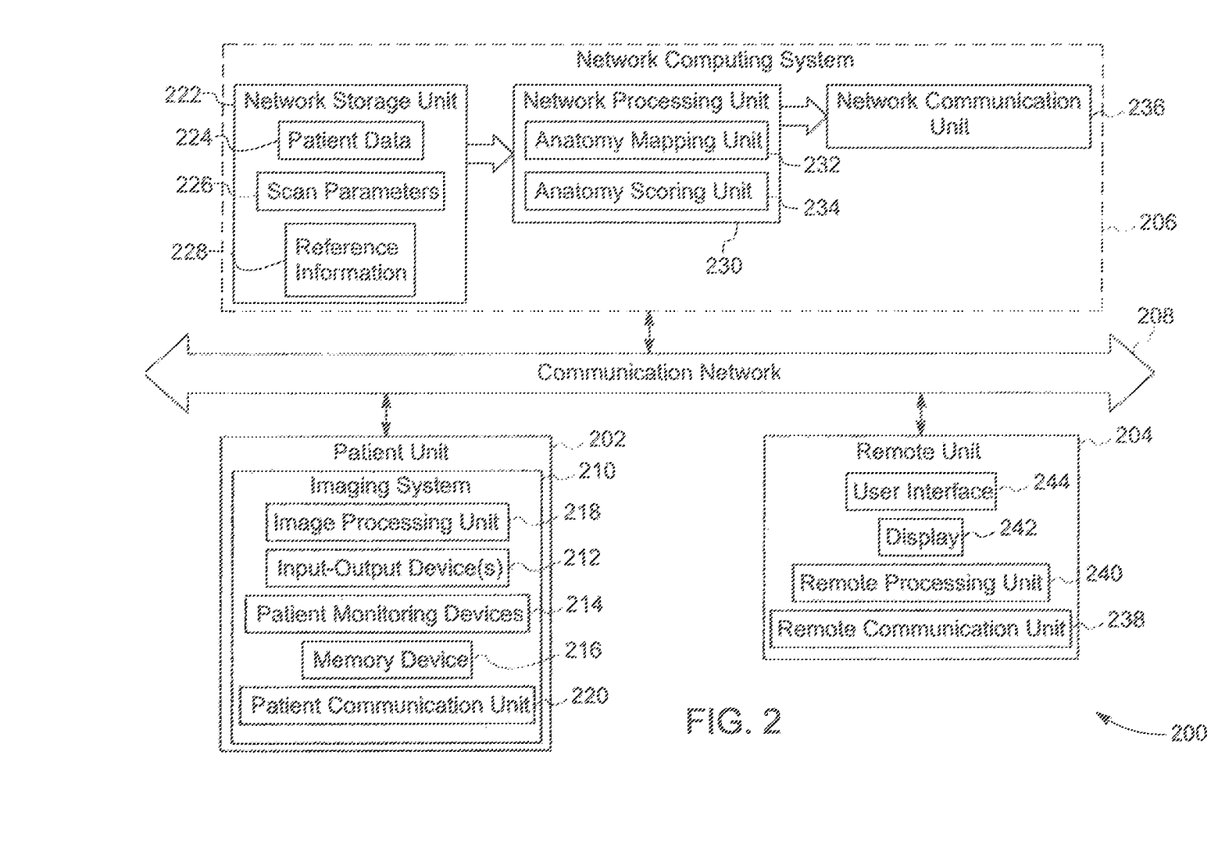
FIG. 2 is a block diagram illustrating exemplary components of a patient data communication system, in accordance with aspects of the present specification.

FIG. 2 illustrates a block diagram illustrating exemplary components of a patient data communication system 200, such as the system 100 of FIG. 1, for use in communicating medically useful information from a patient to a specialist. To that end, in one embodiment, the system 200 may include a patient unit 202, such as the patient unit 102 of FIG. 1. Further, the system 200 may include a remote unit 204, such as the remote unit 104 of FIG. 1, and a network computing system 206, such as the network computing system 106 of FIG. 1. The patient unit 202, the remote unit 204, and the network computing system 206 may be communicatively coupled over a communication network 208, such as the communication network 108 of FIG. 1.

In certain embodiments, the patient unit 202 may include an imaging system 210 configured to acquire imaging data corresponding to a patient. The imaging system 210, for example, may include a CT system, an MRI system, an ultrasound system, a PET scanner, a SPECT scanner, and MR-CT scanner, an MR-PET scanner, and/or an X-ray system. In one embodiment, the imaging system 210 may further include one or more input-output devices 212 configured to allow a user to input scan parameters for imaging a desired region of interest (ROI) of the patient. In one example, the input-output devices 212 may include an interface bank, a control panel, a keyboard, a mouse, a joystick, a touch screen, an audio device, a video device, and/or a display. The interface bank may be configured to function as an integrated set of input-output (I/O) data ports that facilitate easy integration and interoperability of the one or more devices connected to or integrated within the patient unit 202.

Additionally, the input-output devices 212 may also include a graphical user interface (GUI) that may provide the user with selectable options for defining the scan parameters. The scan parameters, for example, may include a type of scan, a selection of the ROI, a pulse sequence, one or more view angles, one or more system parameters, and/or a desired scanning time. In certain embodiments, the GUI may include further options that may be selected to configure the patient unit 202 to transmit select patient data and/or any other medically relevant information to a remotely located specialist.

In one embodiment, the patient unit 202 may further include one or more patient monitoring devices 214, such as the medical devices 112 of FIG. 1 for monitoring the patient. Particularly, the patient monitoring devices 214 may be configured to monitor physiological information and/or ambient environment indicators such as temperature, light, sound, and/or pressure that may affect patient health and/or recovery. In certain embodiments, the system 200 may be configured to store the monitored physiological and environmental information along with the imaging data acquired by the imaging system 210 as patient data in a memory device 216. The memory device 216, for example, may include storage devices such as a random access memory, a read only memory, a disc drive, solid-state memory device, and/or a flash memory.

Alternatively, the system 200 may be configured to communicate the patient data to an image processing unit 218 for further processing. The image processing unit 218 may be configured to determine medically relevant patterns from the patient data and reference information received from the memory device 216. The reference information, for example, may include one or more previous medical reports of the patient, one or more previous images corresponding to the patient, and/or patient profile information. The reference information may further include historical information corresponding to one or more other patients. These other patients may correspond to a similar demographic as the patient under investigation. Further, the reference information may include historical information corresponding to one or more scan parameters used to image the other patients belonging to the similar demographic.

In certain embodiments, the image processing unit 218 may also be configured to receive raw imaging data acquired by the imaging system 210 and generate corresponding images. To that end, the image processing unit 218, for example, may include devices such as one or more general-purpose or application-specific processors, digital signal processors, microprocessors, microcomputers, microcontrollers, Application Specific Integrated Circuits (ASICs), Field Programmable Gate Arrays (FPGA), or other suitable devices.

Further, the image processing unit 218 may be configured to transmit the generated images along with the scan parameters and/or the reference information to the remote unit 204 over the communication network 208. Alternatively, in embodiments where computationally intensive processes are implemented at the network computing system 206, the image processing unit 218 may be configured to transmit the raw imaging data received from the imaging system 210 along with the scan parameters and/or the reference information to the network computing system 206.

In one embodiment, the image processing unit 218 may be configured to employ a patient communication unit 220 for communicating information to the remote unit 204 and/or the network computing system 206. To that end, the patient communication unit 220, for example, may include a radio frequency (RF) transceiver that may be configured to transmit and receive information over the communication network 208. Additionally, the RF transceiver may employ one or more filters, amplifiers, and/or converters to customize the patient data, the scan parameters, and/or the reference information into formats suitable for transmission.

Moreover, in certain embodiments, the patient communication unit 220 may further include devices for providing location determining, authentication, encryption, and/or decryption capabilities. Accordingly, in an exemplary implementation, the patient communication unit 220 may be configured to provide symmetric and/or asymmetric encryption to facilitate secure communication between the patient unit 202, the remote unit 204, and/or the network computing system 206.

In one embodiment, the network computing system 206 may include a network storage unit 222 configured to store information received from the patient unit 202. The received information, for example, may include the patient data, the scan parameters, and/or the reference information. The patient data may generally be represented by reference numeral 224, while reference numeral 226 may be used to refer to the scan parameters. Further, reference numeral 228 may be employed to refer to the reference information. The network storage unit 222, in one example, may be configured to store the patient data 224, the scan parameters 226, and/or the reference information 228 as correlated EMR that may be remotely accessible to authorized persons and/or systems.

Further, the network computing system 206 may include a network processing unit 230. The network processing unit 230 may be configured to receive patient information from the network storage unit 222 for further processing. In the embodiments where the computationally intensive processes are implemented at the network computing system 206, the network processing unit 230 may be configured to reconstruct images using the patient data 224 received from the patient communication unit 220.

Additionally, in certain embodiments, the network processing unit 230 may be configured to identify one or more anatomical regions in each reconstructed image. Particularly, the network processing unit 230 may be configured to detect and/or classify different anatomical regions in the reconstructed image. Accordingly, the network processing unit 230 may include an anatomy mapping unit 232 configured to employ anatomical region detection methods for detecting and/or classifying the anatomical regions in the reconstructed image. In one embodiment, the anatomical region detection methods for use in detecting and/or classifying the anatomical regions in the reconstructed image may be stored in the network storage unit 222.

For example, the anatomy mapping unit 232 may be configured to use the anatomical region detection methods to identify the heart, the liver, and the lungs as the anatomical regions in an image corresponding to a thorax of the patient. To that end, the anatomical region detection methods, for example, may include one or more segmentation algorithms, atlas-based classification, and/or model-based mapping. Additionally, in certain embodiments, the anatomical region detection methods may also entail use of the scan parameters 226 and/or the reference information 228 that may be indicative of anatomical regions of the patient that were imaged previously. Once the anatomical regions in the image are identified, the anatomy mapping unit 232 may also be configured to segment the image into one or more portions such that each portion includes one or more identified anatomical regions. Particularly, in certain embodiments, the anatomy mapping unit 232 may be configured to segment the image into the one or more portions based on a bandwidth of an available communication link in the communication network 208.

Further, in one embodiment, the network processing unit 230 may also include an anatomy scoring unit 234. The anatomy scoring unit 234 may be configured to compute a rank corresponding to each of the identified anatomical regions. The computed rank may be indicative of a relevance of a corresponding anatomical region to patient diagnosis. Accordingly, in one embodiment, the anatomy scoring unit 234 may be configured to determine the relevance of an anatomical region based on the patient data 224, the scan parameters 226, the reference information 228, expert knowledge of the specialist, and/or network characteristics. In particular, the anatomy scoring unit 234 may be configured to evaluate the scan parameters 226, the expert knowledge, the network characteristics, the patient data 224, and/or the reference information 228 to determine the anatomical region that may be of highest relevance for diagnosing the patient, and generate a corresponding rank.

In certain embodiments, for example, the anatomy scoring unit 234 may be configured to determine the relevance of the anatomical region based on a request received from the specialist for a specific ROI. Alternatively, the anatomy scoring unit 234 may be configured to determine the relevance of the anatomical region based on inputs received from a user via the input-output devices 212. Further, the anatomy scoring unit 234 may be configured to determine the relevance of the anatomical region based on the patient data 224 such as current or previous images and/or previous patient reports that may be indicative of the anatomical regions under investigation. In certain other embodiments, the anatomy scoring unit 234 may be configured to determine relevance of the anatomical region based on the scan parameters 226 such as a pulse sequence, view angles, and/or the reference information 228 such as historical information corresponding to other patients belonging to a similar demographic.

Moreover, in one embodiment, the relevance of the anatomical region may be determined subsequent to the segmentation of the image into one or more portions. In an alternative embodiment, however, the anatomy scoring unit 234 and the anatomy mapping unit 232 may be configured to collaborate to determine a relevance of the anatomical regions and segment the image based on the determined relevance. Specifically, the anatomy scoring unit 234 may be configured to identify an order of relevance of the identified anatomical regions, and compute corresponding ranks Further, the anatomy mapping unit 232 may be configured to segment the image such that anatomical regions of similar relevance or ranks may be included in a single portion based on the bandwidth of the available communication link.

Further, the network computing system 206 may include a network communication unit 236. In one embodiment, the network communication unit 236 may be similar to the patient communication unit 220. Moreover, the network communication unit 236 may be configured to transmit the one or more portions of the image to the remote unit 204 based on the computed ranks. To that end, the network communication unit 236 may be configured to measure the network characteristics. The network characteristics, for example, may include a bit rate, latency, jitter, retries, packet sizes, lost packets, and packet errors that may allow the network communication unit 236 to transmit the image portions on a suitable communication channel. Additionally, the network computing unit 236 may also be configured to schedule transmission of the one or more portions of the image to the remote unit 204 based on the computed ranks and/or the measured network characteristics.

Additionally, in one embodiment, the network communication unit 236 may also be configured to use designated authentication, authorization, and security protocols to establish a secure communication channel. Specifically, the network communication unit 236 may be configured to use the secure communication channel for transmission of the portions of the image from the network computing system 206 to the remote unit 204 located at a remote location based on the corresponding ranks However, a communication channel of a suitable bandwidth may not be available at all remote locations. Accordingly, the network processing unit 230 may be configured to modify the image portions, for example through compression and/or interleaving. Particularly, the network processing unit 230 may be configured to modify the image portions such that the modified image portions may be suitable for transmission over an available communication link in the communications network 208. In one example, when diagnosing a patient afflicted with severe chest pains, the network processing unit 230 may be configured to identify one or more portions of the image that correspond to the heart. Further, the network processing unit 230 may be configured to allow for prioritized transmission of portions of the image corresponding to the heart followed by portions of the image corresponding to other anatomical regions in a foreground and/or a background of the image. In certain embodiments, the network processing unit 230 may be configured to compress background regions of the image for transmission over a communication link having limited bandwidth.

Further, in certain embodiments, the network communication unit 236 may be configured to continually monitor a state of a connection between the network computing system 206 and the remote unit 204. In addition, the network communication unit 236 may be configured to ensure re-establishment of a dropped connection between the network computing system 206 and the remote unit 204. In such a scenario, the network communication unit 236 may further be configured to notify the patient unit 202 and/or the remote unit 204 about the state of the connection between the network computing system 206 and the remote unit 204. Additionally, the network communication unit 236 may also be configured to notify the patient unit 202 and/or the remote unit 204 about remedial actions being undertaken for re-establishing any dropped connections.

In one embodiment, the remote unit 204 may include a remote communication unit 238, a remote processing unit 240, a display 242, and a user interface 244. The remote communication unit 238 may be configured to receive communications regarding the state of the connection between the network computing system 206 and the remote unit 204 along with portions of the image from the network communication unit 236. Accordingly, the network communication unit 236 may be communicatively coupled to the remote unit 204 and to the remote communication unit 238 in particular to facilitate this communication.

Additionally, the remote communication unit 238 may further be configured to transmit the received communication and the portions of the image to the remote processing unit 240. In one embodiment, the remote processing unit 240 may be configured to incrementally display the received information on an associated display 242 based on an order in which the portions of the image are received at the remote unit 204. Alternatively, the remote processing unit 240 may be configured to combine two or more portions of the image and render the combined portions on the display 242 simultaneously.

In certain embodiments, the remote unit 204 may further include the user interface 244 to allow the specialist to indicate a desired ROI corresponding to portions of the image rendered on the display 242. By way of example, when receiving an image corresponding to an EKG waveform, the specialist may employ the user interface 244 to indicate the desired ROI by marking a circle around an appropriate location on received portions of the EKG waveform. The remote unit 204 may be configured to transmit the ROI information back to the patient unit 202 directly and/or through the network computing system 206. In one example, the patient unit 202 may be configured to subsample EKG image data and transmit the desired ROI area of the EKG waveform to the remote unit 204 with a relatively higher resolution.

Alternatively, the user interface 244 may be configured to allow the specialist to define parameters for a subsequent scan of one or more desired ROIs. In accordance with aspects of the present specification, the patient unit 202 and/or the network computing system 206 may be configured to prioritize transmission of one or more portions of an image acquired in the subsequent scan based on the specialist's inputs.

Embodiments of the present system 200, thus, allow for optimal transmission of the diagnostic images to a specialist over an available communication channel. Specifically, the system 200 allows for incremental transmission of one or more portions of the diagnostic images over a bandwidth-constrained communication channel based on the ranks corresponding to the anatomical regions. The ranks corresponding to the different portions of the image may be indicative of a relevance of the corresponding anatomical region to patient diagnosis as defined by a specialist, historical information, and/or a specific investigation of the patient being undertaken. The incremental transmission of the diagnostic images expedites availability of the most relevant information to the specialist, which in turn, allows for faster diagnosis and/or treatment of the patient. An exemplary method for expedited transmission of diagnostic images and other medically useful information will be described in greater detail with reference to FIG. 3.

Figure 3:
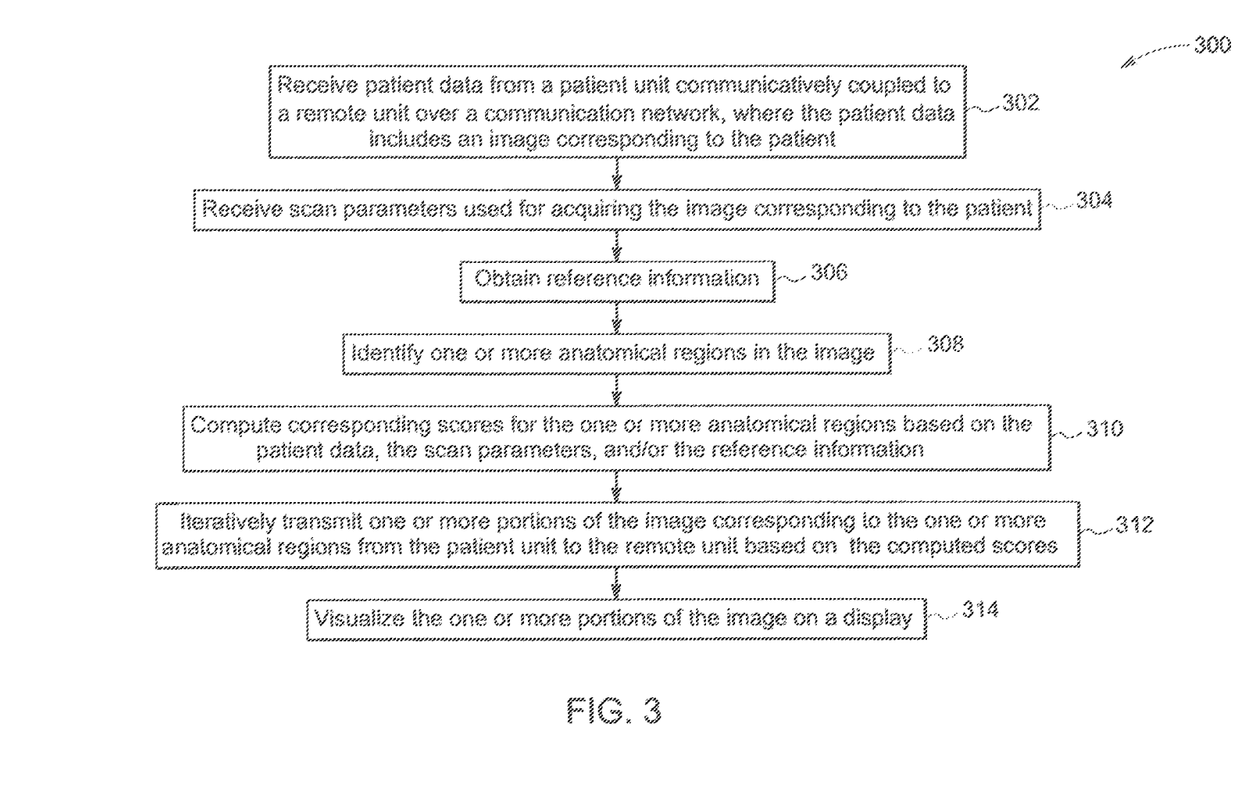
FIG. 3 is a flow chart illustrating an exemplary method for communicating medical data, in accordance with aspects of the present specification.

FIG. 3 illustrates a flow chart 300 depicting an exemplary method for communicating medical data. In the present specification, embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract data types.

Additionally, embodiments of the exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 3, the exemplary method is illustrated as a collection of blocks in a logical flow chart, which represents operations that may be implemented in hardware, software, or combinations thereof. The various operations are depicted in the blocks to illustrate the functions that are performed, for example, during the steps of receiving patient data, anatomical region identification, rank computation, and/or iterative transmission phases of the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-2.

Embodiments of the present specification allow for expedited transmission of patient data to a remotely located specialist. Particularly, the embodiments described herein allow for incremental transmission of portions of diagnostic images that include one or more anatomical regions based on a relevance of the anatomical region for diagnosing a patient. The relevance of the anatomical regions may be determined, for example, based on received patient data, historical patient information, and/or specific requests of the specialist, thereby allowing the specialist to receive the most relevant information first.

In an exemplary patient workflow, each new patient may be assigned a unique identification (UID) in a HIS, for example, using a local system such as the patient unit 202 of FIG. 2. Further, patient medical history may be entered and appended to the patient UID to generate patient data and/or reference information. The reference information may include previously determined information, such as past medical history, diagnostic images, examination reports, consultation notes, and/or profile information such as age, sex, and lifestyle corresponding to the patient. In certain embodiments, the reference information may be used to classify the patient into a particular demographic of one or more other patients.

Further, the reference information and/or the generated patient data associated with the patient UID may be transferred to a database on a local and/or a virtual storage environment like a cloud-based storage system. Additionally, one or more scan parameters used to acquire images corresponding to the patient may also be associated with the patient UID and sent to the cloud-based storage system. In certain embodiments, the patient data, the reference information, and/or the scan parameters may be transferred to the cloud-based storage system in real-time as and when the patient undergoes any diagnostic exam and/or consults a medical practitioner. Alternatively, the patient data, the reference information, and/or the scan parameters may be transferred to the cloud-based storage system at determined intervals of time.

An exemplary implementation of the present method begins at step 302, where patient data is received from a patient unit (see patient unit 202 of FIG. 2) that may be communicatively coupled to a remote unit (see remote unit 204 of FIG. 2) over a communication network (see communication network 208 of FIG. 2). As previously noted, the received patient data may include diagnostic images, previous patient reports, and/or patient profile information such as patient identifier, age, sex, and/or demographics. Further, the patient data may include physiological information such as heart rate and respiration rate received from one or more medical devices that are operatively coupled to the patient.

For discussion purposes, the present embodiment is described with reference to transmission of different portions of a diagnostic image corresponding to different anatomical regions, in accordance with aspects of the present specification. Typical diagnostic images generated using an imaging system (see imaging system 210 of FIG. 2) such as an MRI system may be about one gigabyte (GB) in size. The diagnostic images, thus, may not be suitable for transmission over unpredictable and/or bandwidth-constrained communication channels typically employed by mobile devices such as smartphones and tablets. Difficulty in transmitting the diagnostic images over the bandwidth-constrained communication channels may severely hinder implementation of telemedicine applications. Accordingly, embodiments of the present method allow for efficient and expeditious transmission of patient data to a remotely located specialist.

Further, at step 304, scan parameters may be received. In one embodiment, the scan parameters may be received by the patient unit 202. Alternatively, the scan parameters may be received by a network computing system such as the network computing system 206 of FIG. 2. Moreover, as previously noted, the scan parameters, for example, may include a type of scan, a selection of the ROI, a pulse sequence, one or more view angles, one or more system parameters, and/or a desired scanning time. Thus, in one embodiment, the scan parameters used for acquiring the image corresponding to the patient may provide indication of an anatomical region of the patient that is being imaged. Specifically, the scan parameters and/or past medical history associated with the patient UID may be used to identify a specific type of scan used to image the patient. In one example, decision trees stored in the cloud-based storage system may be used to identify the specific scan, for example, as a cardiac scan. The decision trees may aid in identifying the scan based on scan parameters of a current scan of the patient and/or similar scans performed on other patients associated with a similar demographic as the patient.

Additionally, at step 306, reference information may be obtained. In one embodiment, the reference information may be obtained from the patient unit or from a network device such as the network storage unit 222 of FIG. 2. As previously noted, the reference information may include one or more previous medical reports of the patient, one or more previous images corresponding to the patient, and/or patient profile information. In certain embodiments, the reference information may further include historical information corresponding to other patients associated with a similar demographic, and/or historical information corresponding to one or more scan parameters used to image the other patients. Moreover, in one embodiment, the reference information may allow correlation of known pathological conditions of similar patients with current patient data, thereby aiding in a faster and a more comprehensive diagnosis of the patient.

In addition, at step 308, one or more anatomical regions in the image may be identified. In one embodiment, the anatomical regions may be identified using the scan parameters and/or the reference information that may be indicative of an imaged region of the patient. Further, in certain embodiments, various anatomical region detection methods, for example, one or more segmentation algorithms, atlas-based classification, and/or model-based mapping corresponding to different anatomical regions may be employed for identifying the different anatomical regions in the imaged region. In one embodiment, these anatomical region detection methods may be stored on the cloud-based storage system and may be accessed as described to identify the anatomical regions in the image.

Moreover, in one example, when a liver is identified as an anatomical region in a diagnostic image, a heuristic algorithm stored on the cloud-based storage system may be used to detect and/or localize a hepatic carcinoma in a liver of the patient. In another example, a stored model-based mapping of a thoracic image of a patient may be performed to identify the heart, the liver, and the lungs in the image. Once the anatomical regions in the image are identified, the image may be segmented into one or more portions such that each portion includes one or more of the identified anatomical regions. Particularly, in certain embodiments, the image may be segmented into the one or more portions based on a bandwidth of an available communication link in the communication network.

Further, ranks corresponding to the one or more anatomical regions may be computed, as depicted by step 310. The computed rank, in one embodiment, may be based on based on the patient data, the scan parameters, and/or the reference information. In accordance with aspects of the present specification, the computed rank may be indicative of a relevance of the identified anatomical regions to patient diagnosis. Accordingly, in one embodiment, the relevance of the anatomical regions may be determined based on expert knowledge from a specialist that may be used to rank different anatomical regions. Additionally, the relevance of the anatomical regions may be determined based on patterns determined from stored a priori information (for example, reference information). The a priori information may include medically useful information corresponding to other patients associated with a similar demographic, past patient history and/or present patient data. In certain embodiments, the relevance of the anatomical regions may be determined as a summation of ranks determined from expert knowledge and a priori information.

In certain other embodiments, the corresponding ranks for the anatomical regions may be computed based on a type of data being transmitted, situational dependence, and/or required compression. Additionally, the system may be configured to compute the ranks corresponding to the anatomical regions based on an emergency or non-emergency nature of the transmission. By way of example, for diagnosing a patient who has suffered partial paralysis on his or her left side, a portion of a cerebral image corresponding to the right side of the brain may be assigned the highest rank followed by other portions of the image corresponding to the cerebral and/or spinal regions. Similarly, when assessing a growth and well-being of a fetus using an ultrasound image, one or more portions of the image that correspond to the femur may be assigned the highest rank.

It may be noted that, in one embodiment, the relevance of the anatomical region may be determined subsequent to the segmentation of the image into one or more portions. In an alternative embodiment, however, relevance of the anatomical regions in the image may be determined prior to segmenting the image based on the determined relevance. Specifically, the determined relevance of each of the anatomical regions may define a relative rank or a determined score corresponding to each of the identified anatomical regions in the image. In accordance with aspects of the present specification, the image may be segmented such that anatomical regions having similar ranks may be included in a single portion or in different portions of the image based on the bandwidth of an available communication link.

Further, at step 312, one or more portions of the image corresponding to the one or more anatomical regions may be iteratively transmitted from the patient unit to the remote unit based on the computed ranks To that end, in one embodiment, one or more network characteristics corresponding to one or more communication channels may be determined. Moreover, a portion of the image corresponding to the anatomical region determined to have the highest relevance may be prioritized for transmission over a communication channel with a desired bit rate to ensure a desired quality of the portion of the image on receipt at the remote unit. For example, for a patient who has suffered a cerebral stroke, portions of a cerebral image corresponding to a relevant hemisphere may be prioritized for transmission followed by other portions of the image corresponding to surrounding structures in a foreground of the image.

However, if a suitable communication link having adequate bandwidth is not available to transmit even portions of the image having a desired resolution, an initial low-resolution transmission of the image may be initiated. For example, in one embodiment, an EKG waveform may be transmitted initially with a low quality and resolution along with a notification to the specialist to select a desired ROI on the EKG waveform. The specialist may use a control panel and/or the display on the remote unit to indicate the desired ROI such as an R-interval of the EKG waveform. By way of example, the specialist may select the ROI using a free-form shape around an appropriate location on the received image of the EKG waveform. Further, the remote unit may be configured to transmit the delineated ROI information back to the patient unit. The patient unit may be configured to subsample the EKG image data and transmit the desired ROI area of the EKG waveform with a relatively higher resolution over the communication link having limited bandwidth to the remote unit.

Alternatively, in certain embodiments, ad-hoc multi-hop communication links may be used to communicate high priority patient data expeditiously to the remote unit. To that end, availability of appropriate communication links and corresponding characteristics may be determined in a vicinity of the patient unit and/or the remote unit. In case of limited network connectivity, other available systems such as a WiMax or WiFi network may be tracked. Further, the tracked networks may be used to set up a transmission channel to allow iterative and incremental communication of the patient data between the patient unit and the remote unit. The iterative and incremental communication allows swift provision of specialized medical care to a patient who may be in urgent need of medical assistance.

Furthermore, in certain embodiments, portions of the image corresponding to only a subset of the identified anatomical regions may be transmitted. This subset of the identified anatomical regions may correspond to features whose relevance to a particular patient diagnosis is greater than a determined threshold. For example, when imaging the heart, certain anatomical regions in the image such as the pancreas may be assigned a lower relevance, and thus a lower rank. If a rank corresponding to an anatomical region is lower than a determined threshold value for a specific patient evaluation, one or more image portions corresponding to the anatomical region may not be transmitted. Conversely, only portions of the image corresponding to the high scoring anatomical regions may be iteratively transmitted to the remote unit.

Moreover, at step 314, the one or more portions of the image may be visualized on a display. Particularly, the one or more portions of the image may be visualized on the display of the remote unit iteratively in real-time. To that end, in one embodiment, a remote processing unit such as the remote processing unit 240 of FIG. 2 may be configured to generate a composite image of a previously rendered portion and a currently received portion of the image. Particularly, the remote processing unit 240 may be configured to continually generate and visualize the composite image on the display as the portions of the image are iteratively received at the remote unit. In accordance with aspects of the present specification, a portion of the image including the most relevant anatomical region may be visualized first followed by other anatomical regions and background regions that are incrementally added to the image visualized on the display after each iteration.

The specialist may use the information received and visualized iteratively and incrementally at the remote unit for diagnosing the health of the patient. In certain embodiments, the remote unit may allow the specialist to forward the iteratively received information to another medical professional for seeking a second opinion, thus allowing for provision of quality medical services to the patient irrespective of a location of the specialist and/or the patient. An exemplary sequence of transmission of patient data in accordance with aspects of the present specification will be described in greater detail with reference to FIG. 4.

Figure 4:
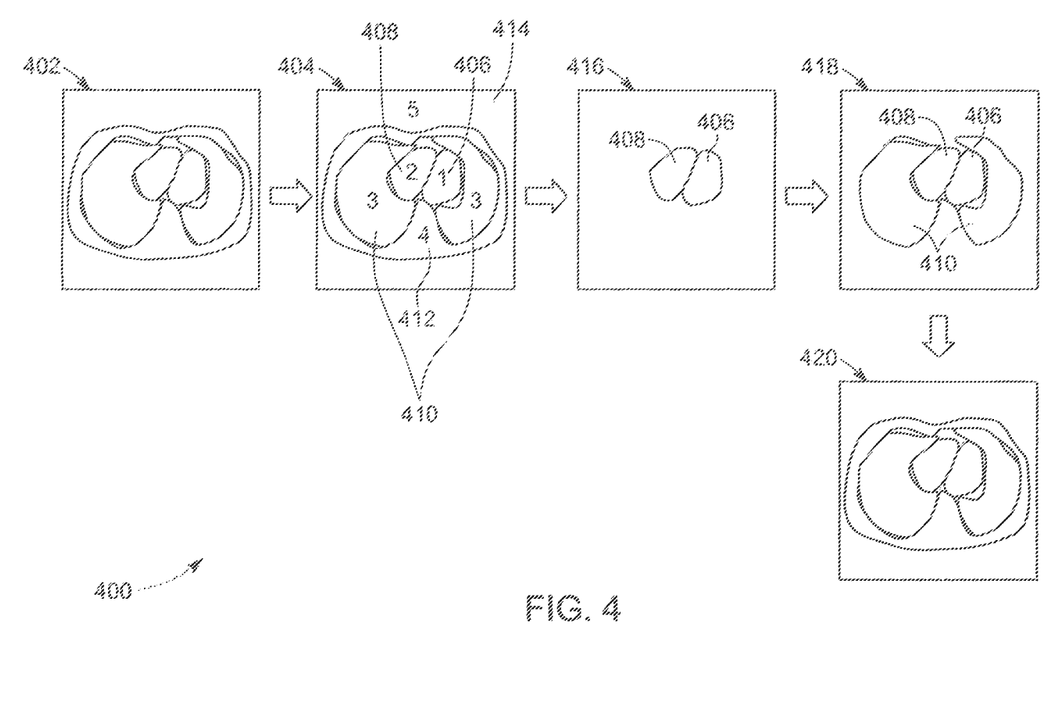
FIG. 4 is a diagrammatical representation depicting an exemplary sequence of transmission of portions of an image using the exemplary method of FIG. 3, in accordance with aspects of the present specification.

FIG. 4 is a diagrammatical representation depicting an exemplary sequence 400 of transmission of portions of an image using the exemplary method of FIG. 3. For clarity, the sequence 400 of transmission of the portions of the image will be described with reference to an exemplary scenario. In the exemplary scenario, a patient suffering from chest pains may be been admitted to a clinic and may be assigned a UID. It may be noted that different pathological conditions such as arrhythmia, a heart attack, or acidity may cause chest pains. An appropriate treatment to be prescribed to the patient may depend upon the pathological condition determined to be an actual cause of the chest pains. Accordingly, the patient may undergo, for example, an MRI scan using the patient unit to generate an image 402 of the thorax of the patient. The image 402 may aid in determining a pathological condition that may be causing the chest pains.

In accordance with aspects of the present specification, the image 402, along with other patient data and/or reference information associated with the patient may be transferred to a database on a local and/or a virtual storage environment. In a presently contemplated embodiment, the database may reside in a cloud-based storage system and/or a cloud computing system. Additionally, one or more scan parameters used to acquire the image 402 may also be associated with the patient UID and communicated to the cloud-based storage system. In certain embodiments, the patient data, the reference information, and/or the scan parameters may be transferred to the cloud-based storage system in real-time. Alternatively, the patient data including the image 402, the reference information, and/or the scan parameters may be transferred to the cloud-based storage system at determined intervals of time.

In a scenario where an experienced cardiologist may be unavailable at the clinic, determining the correct pathological condition using the image 402 may be difficult. In such a scenario, a caregiver available locally may configure the patient unit to communicate the image 402 to a specialist located in a remote location. As previously noted, a communication link having an adequate bandwidth for transmitting the image 402 from the patient unit to the remote unit may not be available at all remote locations. Accordingly, embodiments of the present specification allow for prioritized and incremental transmission of portions of the image 402 to suit the bandwidth of the available communication link.

Accordingly, one or more anatomical regions in the image 402 may be identified. As previously noted, the anatomical regions may be identified, for example, using information derived from the scan parameters, one or more segmentation algorithms, atlas-based classification, and/or model-based mapping. In one example, a model-based mapping of the thoracic region of the patient may allow for identification of the left ventricle of the heart, the right ventricle of the heart, the lungs, the diaphragm, and/or background regions.

Additionally, the image 402 may be segmented such that each segmented portion of the image 402 corresponds to one of the identified anatomical regions. In FIG. 4, a diagrammatical representation of the segmented image may be represented using the reference numeral 404. In the segmented image 404, the reference numeral 406 is used to represent a portion of the image corresponding to the left ventricle and reference numeral 408 is used to represent a portion of the image corresponding to the right ventricle. Further, reference numeral 410 is used to represent portions of the image corresponding to the lungs, while reference numeral 412 is used to represent the portion of the image corresponding to the diaphragm. Additionally, reference numeral 414 is used to represent a portion of the image corresponding to the background regions. Although FIG. 4 depicts each portion of the image as including one identified anatomical region, in alternative embodiments, a portion of the image may include more than one anatomical region depending upon a bandwidth of the available communication link.

Further, a rank corresponding to each of the identified anatomical regions may be computed. As previously noted, the rank may correspond to a relevance of the anatomical region to the patient diagnosis. In one embodiment, the relevance of the anatomical regions may be determined, for example, based on a scan type determined using the scan parameters, a request received from the specialist and/or medical history of the patient.

In one example, if the specialist requests for information corresponding to the left and right ventricles of the heart, the corresponding portions 406 and 408 of the image 404 may be determined to be the first and second most relevant anatomical regions and a corresponding rank may be determined. Further, the medical history of the patient may indicate that the lungs may correspond to the anatomical regions of some interest. Accordingly, the portion 410 of the image corresponding to the lungs may be ranked as the third most relevant anatomical region in the image 404. Similarly, the portions 412 and 414 of the image 404 corresponding to the diaphragm and the background regions may be determined to be the fourth and fifth most relevant anatomical regions in the image 404. Accordingly, a rank corresponding to each anatomical region may be assigned based on the determined relevance.

In the embodiment depicted in FIG. 4, the rank corresponding to each anatomical region may be representative of an order of transmission of the portion of the image corresponding to the anatomical region. In certain embodiments, the segmentation and/or scoring of the portions of the image may be performed by the network computing unit. However, in alternative embodiments, the segmentation and/or scoring of the portions of the image may be performed by the patient unit.

Further, in accordance with aspects of the present specification, the different portions of the image 404 may be transmitted to the remote unit based on the computed rank. Thus, the portions 406 and 408 of the image 404 corresponding to the left ventricle and the right ventricle, respectively, may be transmitted to the specialist in a first iteration. Reference numeral 416 may be representative of a visualization of the portions 406 and 408 of the image 402 corresponding to the left ventricle and the right ventricle once these are received at the remote unit. The specialist may be able to determine a pathological condition of the patient, for example an infarction in the left or right ventricles of the heart, based on the portions of the image visualized on the remote unit after the first iteration. The specialist, thus, may be able to make an initial diagnosis and prescribe immediate treatment for the patient without having to wait for receipt of the entire image 402.

Moreover, reference numeral 418 may be representative of a composite image generated using the previously visualized portions 406 and 408 corresponding to heart ventricles and subsequently received portions 410 corresponding to the lungs regions. Further, reference numeral 420 may be representative of a composite image that combines and visualizes the heart, lungs, diaphragm, and background regions in a single image on a display of the remote unit. The composite image 420 may be equivalent to the originally acquired image 402, where the composite image 420 may be used by the specialist to determine an accurate cause of the chest pains and prescribe suitable treatment.

Embodiments of the present specification, thus, provide systems and methods that allow for incremental and iterative transmission of patient data, thereby reducing a time to access critical medical information corresponding to a patient. Particularly, use of a virtual server and/or a cloud-based storage and/or cloud computing system allows switching resource intensive image reconstruction, anatomy classification, and/or prioritization of patient data transmission from a local system to a remote device, thereby saving energy, equipment costs, and/or floor space. Additionally, embodiments of the present method allow for iterative and incremental transmission of medical data that may be sustained even over resource-constrained communication networks. Communications over the resource-constrained networks extend the reach of the present systems and methods over large geographical areas, thereby allowing for patients anywhere to receive quality medical services irrespective of a location of the patient and/or the specialist. Such widespread and real-time access to quality medical care, in turn, allows for improved hospital workflow and faster patient turnaround time.

Although, the embodiments described herein disclose use of a network computing system 206 for computationally intensive processes such as image reconstruction, classification, and/or scoring, in alternative embodiments, the network computing system 206 may be absent. In such embodiments, the functions of the network computing system 206 may be performed by the image processing unit 218 of the FIG. 2 and/or a local or remotely located virtual server. Furthermore, certain embodiments of the present specification may be implemented simultaneously in multiple medical devices as well as multiple imaging systems to facilitate intelligent and multi-directional communication.

It may further be noted that the foregoing examples, demonstrations, and process steps that may be performed by certain components of the present systems, for example by the image processing unit 218, the network processing unit 230, and/or the remote processing unit 240 of FIG. 2, may be implemented by suitable code on a processor-based system. To that end, the processor-based system, for example, may include a general-purpose or a special-purpose computer. It may also be noted that different implementations of the present specification may perform some or all of the steps described herein in different orders or substantially concurrently.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of embodiments of the present specification may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and methods for use in enhanced patient evaluation and management.

While only certain features of the present specification have been illustrated and described herein, many modifications and changes will occur to those skilled in the art. It is, therefore, to be understood that the appended claims are intended to cover all such modifications and changes as fall within the true spirit of the invention.

What is claimed is:

1. A method comprising:
   capturing, by a medical device communicatively coupled to a remote unit over a communication network, patient data of a patient, wherein the patient data comprises at least an image of the patient;
   identifying, by the medical device, anatomical regions in the image;
   segmenting, by the medical device, the image into respective portions corresponding to the anatomical regions;
   measuring, by the medical device, at least one network characteristic of the communication network, wherein the at least one network characteristic comprises at least one of bandwidth, bit rate, latency, jitter, retries, packet sizes, lost packets, or packet errors;
   computing, by the medical device, respective ranks for the anatomical regions based on the patient data and the at least one network characteristic of the communication network;
   generating, by the medical device, an ordered list of the anatomical regions from highest rank to lowest rank based on the respective ranks of the anatomical regions;
   selecting, by the medical device, a subset of the anatomical regions having ranks exceeding a threshold rank; and
   iteratively transmitting, by the medical device to the remote unit, in ranked order according to the ordered list, communications comprising the respective portions of the image corresponding to the subset of the anatomical regions, wherein the communications initiate the remote device to incrementally display associated respective portions of the image in the ranked order on a display device associated with the remote unit.

2. The method of claim 1, wherein the patient data further comprises one or more physiological parameters measured by the mobile medical device, and wherein the respective ranks are further based on the one or more physical parameters.

3. The method of claim 1, further comprising receiving, by the medical device, scan parameters, wherein the scan parameters comprise at least one of a pulse sequence, one or more view angles, user input, one or more system settings, or a scanning time.

4. The method of claim 1, wherein the remote unit is associated with a medical specialist currently treating the patient.

5. The method of claim 1, wherein identifying the one or more anatomical regions in the image comprises detecting the one or more anatomical regions based on at least one of the patient data, one or more segmentation methods, an atlas-based classification, or a model-based mapping.

6. The method of claim 1, wherein the computing the respective ranks comprises determining a relevance of each of the one or more anatomical regions for diagnosing the patient based on the patient data.

7. The method of claim 6, wherein iteratively transmitting comprises iteratively transmitting the respective portions of the image corresponding to the subset of the anatomical regions at first resolution; and
   further comprising, after iteratively transmitting the respective portions of the image corresponding to the subset, transmitting at a second resolution other portions of the image corresponding to anatomical regions not in the subset, wherein the first resolution is higher than the second resolution.

8. The method of claim 1, wherein iteratively transmitting comprises iteratively transmitting the respective portions of the image corresponding to a subset of the anatomical regions in an uncompressed format; and
   further comprising, after iteratively transmitting the respective portions of the image corresponding to the subset, transmitting in a compressed format other portions of the image corresponding to anatomical regions not in the subset.

9. The method of claim 8, wherein the respective ranks are further based on a determined urgency of a medical condition of the patient based on the patient data.

10. A medical imaging device communicatively coupled to a remote unit over a communication network, the medical imaging device comprising:
    a processor; and
    a memory communicatively coupled to the processor, the memory having stored therein computer-executable instructions, comprising:
      an imaging component configured to capture patient data of the patient,
    wherein the patient data comprises at least an image corresponding to the patient;
      an anatomy mapping unit configured to:
        identify anatomical regions in the image, and
        segment the image into respective portions corresponding to the anatomical regions;
      a network communication unit configured to measure at least one network characteristic of the communication network, wherein the at least one network characteristic comprises at least one of bandwidth, bit rate, latency, jitter, retries, packet sizes, lost packets, or packet errors; and
      an anatomy scoring unit configured to:
        compute respective ranks for the anatomical regions based on the patient data and a network characteristic of the communication network,
        generate an ordered list of the anatomical regions from highest rank to lowest rank based on the respective ranks of the anatomical regions, and
        select a subset of the anatomical regions having ranks exceeding a threshold rank; and
      wherein the network communication unit is further configured to iteratively transmit to the remote unit, in ranked order according to the ordered list, communications comprising the respective portions of the image corresponding to the subset of the anatomical regions, wherein the communications initiate the remote device to incrementally display associated respective portions of the image in the ranked order on a display device associated with the remote unit.

11. The medical imaging device of claim 10, wherein the medical imaging device is a mobile medical imaging device.

12. The medical imaging device of claim 10, wherein the network communication unit is further configured to:
    iteratively transmit the respective portions of the image corresponding to the subset of the anatomical regions at first resolution; and after iteratively transmitting the respective portions of the image corresponding to the subset, transmit at a second resolution other portions of the image corresponding to anatomical regions not in the subset, wherein the first resolution is higher than the second resolution.

13. The medical imaging device of claim 10, wherein the network communication unit is further configured to:
iteratively transmit the respective portions of the image corresponding to a subset of the anatomical regions in an uncompressed format; and
after iteratively transmitting the respective portions of the image corresponding to the subset, transmit in a compressed format other portions of the image corresponding to anatomical regions not in the subset.

14. A non-transitory computer-readable medium having instructions stored thereon that, in response to execution, cause a medical imaging device communicatively coupled to a remote unit over a communication network to perform operations comprising:
capturing patient data of a patient, wherein the patient data comprises at least a medical image of the patient;
identifying anatomical regions in the medical image;
segmenting the medical image into respective portions corresponding to the anatomical regions;
measuring at least one network characteristic of the communication network, wherein the at least one network characteristic comprises at least one of bandwidth, bit rate, latency, jitter, retries, packet sizes, lost packets, or packet errors;
computing respective ranks for the anatomical regions based on the patient data and the at least one network characteristic of the communication network;
generating an ordered list of the anatomical regions from highest rank to lowest rank based on the respective ranks of the anatomical regions;
selecting a subset of the anatomical regions having ranks exceeding a threshold rank; and
iteratively transmitting, by the medical device to the remote unit, in ranked order according to the ordered list, communications comprising the respective portions of the medical image corresponding to the subset of the anatomical regions, wherein the communications initiate the remote device to incrementally display associated respective portions of the image in the ranked order on a display device associated with the remote unit.

15. The non-transitory computer-readable medium of claim 14, wherein the medical device is a mobile medical device.

16. The non-transitory computer-readable medium of claim 14, wherein iteratively transmitting comprises iteratively transmitting the respective portions of the medical image corresponding to the subset of the anatomical regions at first resolution; and
the operations further comprise, after iteratively transmitting the respective portions of the medical image corresponding to the subset, transmitting at a second resolution other portions of the medical image corresponding to anatomical regions not in the subset, wherein the first resolution is higher than the second resolution.

17. The non-transitory computer-readable medium of claim 14, wherein iteratively transmitting comprises iteratively transmitting the respective portions of the medical image corresponding to a subset of the anatomical regions in uncompressed format; and
the operations further comprise, after iteratively transmitting the respective portions of the medical image corresponding to the subset, transmitting in compressed format other portions of the medical image corresponding to anatomical regions not in the subset.

* * * * *